(12) United States Patent
Nishijima (10) Patent No.: US 11,510,637 B2
(45) Date of Patent: Nov. 29, 2022

(54) COLLIMATOR AND COLLIMATOR MODULE

(71) Applicant: CANON MEDICAL SYSTEMS CORPORATION, Otawara (JP)

(72) Inventor: Akira Nishijima, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 24 days.

(21) Appl. No.: 17/167,229

(22) Filed: Feb. 4, 2021

(65) Prior Publication Data

US 2021/0282727 A1 Sep. 16, 2021

(30) Foreign Application Priority Data

Mar. 16, 2020 (JP) .............................. JP2020-045857

(51) Int. Cl.
*A61B 6/06* (2006.01)
*A61B 6/00* (2006.01)
*G21K 1/10* (2006.01)
*G21K 1/02* (2006.01)

(52) U.S. Cl.
CPC .............. *A61B 6/06* (2013.01); *A61B 6/4291* (2013.01); *G21K 1/02* (2013.01); *G21K 1/10* (2013.01)

(58) Field of Classification Search
CPC ........... A61B 6/542; A61B 6/488; A61B 6/06; A61B 6/5282; A61B 6/032; A61B 6/4291; G21K 1/02; G21K 2207/005; G21K 1/10
See application file for complete search history.

(56) References Cited

U.S. PATENT DOCUMENTS 8,976,935 B2  3/2015 Singh et al.
2014/0294158 A1 10/2014 Okamoto et al.

FOREIGN PATENT DOCUMENTS

| JP | 7-333395 A | 12/1995 | | |
|----|----|----|----|----|
| JP | 9-257996 A | 10/1997 | | |
| JP | 2006-526761 A | * 11/2006 | ............. | G21K 1/025 |
| JP | 2014-209107 A | 11/2014 | | |
| JP | 2018-96792 A | 6/2018 | | |

* cited by examiner

*Primary Examiner* — Don K Wong
(74) *Attorney, Agent, or Firm* — Oblon, McClelland, Maier & Neustadt, L.L.P.

(57) ABSTRACT

A collimator according to an embodiment is a collimator for use in an X-ray CT apparatus and includes a collimator module and resin. The collimator module includes a first scattered ray eliminating part and a second scattered ray eliminating part. The resin is provided between the first scattered ray eliminating part and the second scattered ray eliminating part and is configured to hold the first scattered ray eliminating part and the second scattered ray eliminating part.

14 Claims, 8 Drawing Sheets

COLLIMATOR AND COLLIMATOR MODULE

CROSS-REFERENCE TO RELATED APPLICATIONS

This application is based upon and claims the benefit of priority from Japanese Patent Application No. 2020-045857, filed on Mar. 16, 2020; the entire contents of which are incorporated herein by reference.

FIELD

Embodiments described herein relate generally to a collimator and a collimator module.

BACKGROUND

Conventionally, X-ray Computed Tomography (CT) apparatuses include an X-ray detector configured to detect X-rays. Generally speaking, such an X-ray detector for use in an X-ray CT apparatus includes a collimator in which a plurality of X-ray blocking plates are arranged in a grid formation, so that the X-ray blocking plates protect X-ray detecting elements from scattered X-rays that may become incident thereto.

DETAILED DESCRIPTION

A collimator according to an embodiment is a collimator for use in an X-ray CT apparatus and includes a collimator module and resin. The collimator module includes a first scattered ray eliminating part and a second scattered ray eliminating part. The resin is provided between the first scattered ray eliminating part and the second scattered ray eliminating part and is configured to hold the first scattered ray eliminating part and the second scattered ray eliminating part.

Embodiments

In the following sections, exemplary embodiments of a collimator and a collimator module of the present disclosure will be explained, with reference to the accompanying drawings. The configurations illustrated in the drawings are schematic. The dimensions of the constituent elements in the drawings and the proportions of the dimensions among the constituent elements may be different from those in actuality. Further, different drawings may illustrate differently the dimensions of the same constituent elements and the proportions of the dimensions among the constituent elements.

In the embodiments described below, examples will be explained in which configurations of the collimator and the collimator module of the present disclosure are applied to an X-ray detector and an X-ray CT apparatus.

Figure 1:
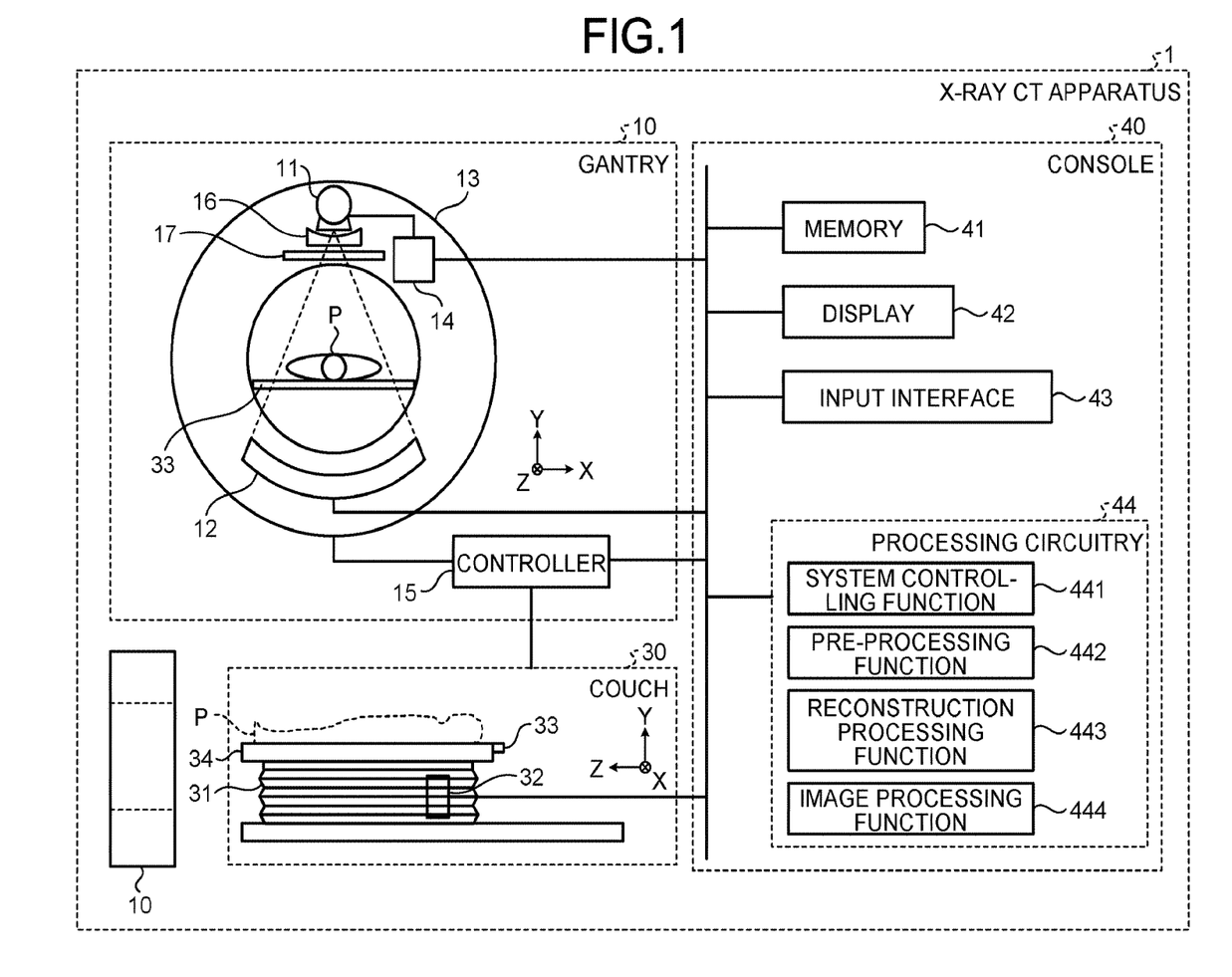
FIG. 1 is a diagram illustrating an exemplary configuration of an X-ray CT apparatus according to an embodiment of the present disclosure.

FIG. 1 is a diagram illustrating an exemplary configuration of an X-ray CT apparatus according to an embodiment of the present disclosure.

For example, as illustrated in FIG. 1, an X-ray CT apparatus 1 according to the present embodiment includes a gantry 10, a couch 30, and a console 40. For the sake of convenience in the explanation, the gantry 10 is depicted more than once in FIG. 1.

In the present embodiment, the rotation axis of a rotating frame 13 in a non-tilted state or the longitudinal direction of a couchtop 33 of the couch 30 is defined as a "Z-axis direction". The axial direction orthogonal to the Z-axis direction and parallel to the floor surface is defined as an "X-axis direction". The axial direction orthogonal to the Z-axis direction and perpendicular to the floor surface is defined as a "Y-axis direction".

The gantry 10 is configured to radiate X-rays onto a subject P, to detect X-rays that have passed through the subject P, and to output a detection result to the console 40. The gantry 10 includes an X-ray tube 11, an X-ray detector 12, the rotating frame 13, a controller 15, a wedge 16, an X-ray limiter 17, and an X-ray high-voltage device 14.

The X-ray tube 11 is a vacuum tube configured to generate the X-rays by emitting thermo electrons from a negative pole (a filament) toward a positive pole (a target), with high voltage applied from the X-ray high-voltage device 14. For example, the X-ray tube 11 is a rotating anode X-ray tube configured to generate the X-rays by emitting the thermo electrons onto a rotating anode (positive pole).

The wedge 16 is a filter used for adjusting the dose of the X-rays radiated from the X-ray tube 11. More specifically, the wedge 16 is a filter configured to pass and attenuate the X-rays radiated from the X-ray tube 11, so that the X-rays radiated from the X-ray tube 11 onto the subject P have a predetermined distribution. For example, the wedge 16 is a filter obtained by processing aluminum so as to have a predetermined target angle and a predetermined thickness. The wedge 16 may be referred to as a wedge filter or a bow-tie filter.

The X-ray limiter 17 includes lead plates or the like used for narrowing down the radiation range of the X-rays that have passed through the wedge 16 and is configured to form a slit with a combination of the plurality of lead plates or the like.

The X-ray detector 12 is configured to detect the X-rays that were radiated from the X-ray tube 11 and have passed through the subject P. More specifically, the X-ray detector 12 includes a plurality of rows of detecting elements in each of which a plurality of detecting elements are arranged in a channel direction along an arc centered on a focal point of the X-ray tube 11. For example, the X-ray detector 12 has a structure in which the plurality of rows of detecting elements are arranged in a row direction (which may be called a slice direction), the plurality of rows each having the plurality of detecting elements arranged in the channel direction.

Further, the X-ray detector 12 includes a Data Acquisition System (DAS) configured to process electrical signals output from the detecting elements. The DAS includes an amplifier configured to perform an amplifying process on the electrical signals output from the X-ray detecting elements of the X-ray detector 12; and an Analog/Digital (A/D) converter configured to convert the electrical signals into digital signals. The DAS is configured to generate detection data. The detection data generated by the DAS is transferred to the console 40.

The X-ray high-voltage device 14 includes: a high-voltage generator including electrical circuits such as a transformer, a rectifier, and the like and having a function of generating the high voltage to be applied to the X-ray tube 11; and an X-ray controller configured to control the output voltage in accordance with the X-ray output radiated by the X-ray tube 11. The high-voltage generator may be of a transformer type or of an inverter type. Further, the X-ray high-voltage device 14 may be provided on the rotating frame (explained later) or may be provided on a supporting frame (not illustrated) configured to rotatably support the rotating frame 13 in the gantry 10.

The rotating frame 13 is an annular frame configured to support the X-ray tube 11 and the X-ray detector 12 so as to oppose each other and configured to rotate the X-ray tube 11 and the X-ray detector 12 via the controller 15 (explained later). In addition to supporting the X-ray tube 11 and the X-ray detector 12, the rotating frame 13 further includes and supports the X-ray high-voltage device 14. In this situation, the detection data generated by the DAS included in the X-ray detector 12 is transmitted from a transmitter including a Light Emitting Diode (LED) and being provided on the rotating frame 13, to a receiver including a photodiode and being provided in a non-rotation part (e.g., the supporting frame) of the gantry 10, through optical communication, and is further transferred to the console 40. The method for transmitting the detection data from the rotating frame 13 to the non-rotation part of the gantry 10 is not limited to the optical communication described above and may be realized with any of other contactless data transfer methods.

The controller 15 includes: processing circuitry having a Central Processing Unit (CPU) or the like; and a driving mechanism configured with a motor, an actuator, and/or the like. Upon receipt of an input signal from an input interface 43 attached to the console 40 or to the gantry 10, the controller 15 has a function of controlling operations of the gantry 10 and the couch 30. For example, upon receipt of input signals, the controller 15 is configured to exercise control so as to rotate the rotating frame 13, to tilt the gantry 10, and to bring the couch 30 and the couchtop 33 into operation. In this situation, the control to tilt the gantry 10 is realized as a result of the controller 15 rotating the rotating frame 13 on an axis parallel to the X-axis direction, on the basis of tilting angle (tilt angle) information input through the input interface 43 attached to the gantry 10. The controller 15 may be provided for the gantry 10 or may be provided for the console 40.

The couch 30 is configured so that the subject P to be scanned is placed thereon and configured to move the subject P. The couch 30 includes a base 31, a couch driver 32, the couchtop 33, and a supporting frame 34. The base 31 is a casing configured to support the supporting frame 34 so as to be movable in the vertical directions. The couch driver 32 is a motor or an actuator configured to move the couchtop 33 on which the subject P is placed, along the long axis directions thereof. The couchtop 33 provided on the top face of the supporting frame 34 is a board on which the subject P is placed. In addition to the couchtop 33, the couch driver 32 may also move the supporting frame 34 along the long axis directions of the couchtop 33.

The console 40 is configured to receive operations performed by an operator on the X-ray CT apparatus 1 and to also reconstruct CT image data by using the detection data acquired by the gantry 10. The console 40 includes a memory 41, a display 42, the input interface 43, and processing circuitry 44. In the present example, the console 40 and the gantry 10 are separate from each other; however, another arrangement is also acceptable in which the gantry 10 includes the console 40 or one or more of the constituent elements of the console 40.

The memory 41 is realized by using, for example, a semiconductor memory element such as a Random Access Memory (RAM) or a flash memory, or a hard disk, an optical disk, or the like. For example, the memory 41 is configured to store therein projection data and the CT image data.

The display 42 is configured to display various types of information. For example, the display 42 is configured to output medical images (CT images) generated by the processing circuitry 44, a Graphical User Interface (GUI) used for receiving various types of operations from the operator, and the like. For example, the display 42 is a liquid crystal display or a Cathode Ray Tube (CRT) display. Alternatively, for example, the display 42 may be provided for the gantry 10. Further, for example, the display 42 may be of a desktop type or may be configured by using a tablet terminal or the like capable of wirelessly communicating with the main body of the console 40.

The input interface 43 is configured to receive various types of input operations from the operator, to convert the received input operations into electrical signals, and to output the electrical signals to the processing circuitry 44. For example, the input interface 43 is configured to receive, from the operator, an acquisition condition used at the time of acquiring the projection data, a reconstruction condition used at the time of reconstructing the CT image data, an image processing condition used at the time of generating a post-processing image from a CT image, and the like. For example, the input interface 43 is realized by using a mouse, a keyboard, a trackball, a switch, a button, a joystick, and/or the like. Alternatively, for example, the input interface 43 may be provided for the gantry 10. Further, for example, the input interface 43 may be configured by using a tablet terminal or the like capable of wirelessly communicating with the main body of the console 40.

The processing circuitry 44 is configured to control operations of the entirety of the X-ray CT apparatus 1. For example, the processing circuitry 44 is configured to execute a system controlling function 441, a pre-processing function 442, a reconstruction processing function 443, and an image processing function 444.

The system controlling function 441 is configured to control the various types of functions of the processing circuitry 44, on the basis of the input operations received from the operator via the input interface 43. For example, the system controlling function 441 is configured to control a CT scan performed by the X-ray CT apparatus 1. Further, the system controlling function 441 is configured to control the generation and the display of the CT image data by the console 40, by controlling the pre-processing function 442, the reconstruction processing function 443, and the image processing function 444.

The pre-processing function 442 is configured to generate the projection data obtained by performing pre-processing processes such as a logarithmic conversion process, an offset correcting process, an inter-channel sensitivity correcting process, a beam hardening correction, and/or the like on the detection data output from the DAS included in the X-ray detector 12. The data (the detection data) before the pre-processing processes and the data after the pre-processing processes may collectively be referred to as the projection data.

The reconstruction processing function 443 is configured to generate the CT image data (reconstructed image data) by performing a reconstructing process using a filtered back projection method, a successive approximation reconstruction method, or the like, on the projection data generated by the pre-processing function 442.

On the basis of an input operation received from the operator via the input interface 43, the image processing function 444 is configured to convert the CT image data generated by the reconstruction processing function 443 into tomographic image data or three-dimensional image data on an arbitrary cross-sectional plane, by using a publicly-known method. Alternatively, the three-dimensional image data may directly be generated by the reconstruction processing function 443.

In relation to the above, for example, the processing circuitry 44 is realized by using a processor. In that situation, the processing functions of the processing circuitry 44 are stored in the memory 41 in the form of computer-executable programs. Further, the processing circuitry 44 is configured to realize the functions corresponding to the programs by reading and executing the programs from the memory 41. In other words, the processing circuitry 44 that has read the programs has the processing functions illustrated within the processing circuitry 44 in FIG. 1.

In the present example, the abovementioned processing functions are realized by the single piece of processing circuitry (i.e., the processing circuitry 44); however, it is also acceptable, for example, to structure the processing circuitry 44 by combining together a plurality of independent processors, so that the processing functions are realized as a result of the processors executing the programs. Further, the processing functions of the processing circuitry 44 may be realized as being distributed among, or integrated together in, one or more pieces of processing circuitry, as appropriate. Further, the processing functions of the processing circuitry 44 may be realized by a combination of hardware such as circuits and software. Furthermore, although the example was explained in which the single memory (i.e., the memory 41) stores therein the programs corresponding to the processing functions, possible embodiments are not limited to this example. For instance, another arrangement is also acceptable in which a plurality of storage circuits are provided in a distributed manner, so that the processing circuitry 44 reads and executes a corresponding program from each of the individual storage circuits.

Figure 2:
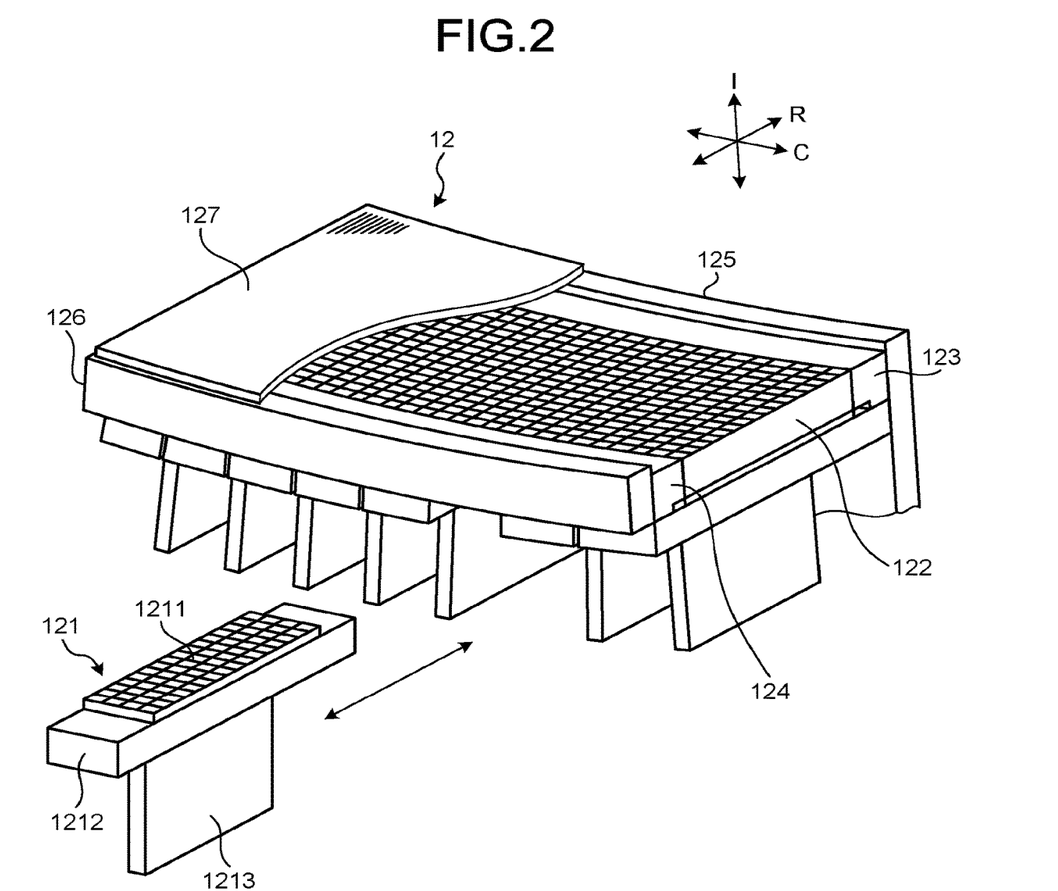
FIG. 2 is a drawing illustrating an exemplary configuration of an X-ray detector according to the present embodiment.

FIG. 2 is a drawing illustrating an exemplary configuration of the X-ray detector 12 according to the present embodiment.

For example, as illustrated in FIG. 2, the X-ray detector 12 is formed to have a substantially arc shape as a whole and is fixed to the rotating frame 13 described above in such a manner that the center of the arc coincides with the position of the X-ray tube 11.

In this situation, the circumferential direction of the arc of the X-ray detector 12 coincides with the channel direction. Further, the axial direction of the arc of the X-ray detector 12 coincides with the row direction. Also, the radial direction of the arc of the X-ray detector 12 coincides with the X-ray radiation direction. In the drawings referenced in the following explanations, the channel direction is indicated with an arrow C, while the row direction is indicated with an arrow R, and the X-ray radiation direction is indicated with an arrow I.

For example, the X-ray detector 12 includes a plurality of X-ray detector modules 121, a collimator 122, a first fixed frame 123, a second fixed frame 124, a first supporting frame 125, a second supporting frame 126, and an optical blocking plate 127.

Each of the X-ray detector modules 121 includes an X-ray detection array 1211, a supporting member 1212, and a DAS 1213.

The X-ray detection array 1211 includes a scintillator array and a photodiode array. The scintillator array includes a plurality of scintillators arranged in the channel direction and the row direction. Each of the scintillators includes a scintillator crystal that outputs light in a photon quantity corresponding to the amount of X-rays being incident thereto. The photodiode array includes, as detecting elements, a plurality of photodiodes arranged in the channel direction and the row direction. The photodiodes included in the photodiode array are arranged so as to be in one-to-one correspondence respectively with the scintillators included in the scintillator array and are each configured to output an electrical signal corresponding to the amount of light being output from the corresponding scintillator to the DAS 1213.

The supporting member 1212 is formed to have a substantially cuboidal shape and has, on the face thereof facing the X-ray tube 11, the X-ray detection array 1211 fixed, so as to support the X-ray detection array 1211.

On another face of the supporting member 1212 opposite from the face having the X-ray detection array 1211, the DAS 1213 is attached so as to extend along the X-ray radiation direction and is configured to generate the detection data on the basis of the electrical signals output from the photodiodes in the X-ray detection array 1211.

The collimator 122 includes a plurality of X-ray blocking plates arranged in a grid formation along the channel direction and the row direction. The X-ray blocking plates protect the X-ray detection arrays 1211 in the X-ray detector modules 121 from scattered X-rays that may become incident thereto. More specifically, the collimator 122 is formed to have a substantially arc shape along the channel direction, so as to cover the X-ray detector modules 121. The X-ray blocking plates are configured to eliminate scattered rays from the X-rays becoming incident to the X-ray detection arrays 1211 in the X-ray detector modules 121.

The first fixed frame 123 and the second fixed frame 124 are fixed to the two ends of the collimator 122 in terms of the row direction. On the side opposite from the X-ray incident side, the plurality of X-ray detector modules 121 are attached while being arranged in the channel direction. In this situation, the first fixed frame 123 and the second fixed frame 124 are configured so that each of the X-ray detector modules 121 can individually be attached thereto and detached therefrom.

The first supporting frame 125 and the second supporting frame 126 are configured to support the collimator 122 and the fixed frames. More specifically, the first supporting frame 125 and the second supporting frame 126 are configured to support the first fixed frame 123, the second fixed frame 124, and the collimator 122 that are sandwiched from the two sides in the row direction. In this state, the structure is fixed to the supporting frame (not illustrated) of the gantry 10.

The optical blocking plate 127 is configured to inhibit light from becoming incident to the X-ray detection arrays 1211 of the X-ray detector modules 121. For example, the optical blocking plate 127 is a member formed as a thin plate by using a material capable of inhibiting light. The optical blocking plate 127 is attached to the first supporting frame 125 and to the second supporting frame 126 so as to cover the entirety of the collimator 122.

Configurations of the X-ray CT apparatus 1 and the X-ray detector 12 have thus been explained. In the present embodiment with these configurations, the X-ray detector 12 includes the collimator in which the plurality of X-ray blocking plates are arranged in the grid formation, as described above.

Generally speaking, collimators in which a plurality of X-ray blocking plates are arranged in a grid formation as described above are known to have high manufacturing costs. For example, known methods include: a method by which X-ray blocking plates are manually inserted into a frame and fixed by using an adhesive or the like while the frame has grooves formed with a high level of precision; and a method by which a collimator is formed by using a three-dimensional (3D) printer. Each of these methods has low throughput and a high cost. Further, generally speaking, because molybdenum or the like used as a material of X-ray blocking plates has low processability, when the pitch between the X-ray blocking plates needs to be smaller to accommodate a highly detailed configuration of X-ray detectors, the manufacture becomes more difficult, which makes the manufacturing cost higher.

To cope with these circumstances, the present embodiment makes it possible to reduce the manufacturing cost of the collimator 122 for use in an X-ray CT apparatus.

More specifically, in the present embodiment, the collimator 122 includes the plurality of collimator modules arranged in the channel direction. Further, each of the collimator modules includes: the plurality of X-ray blocking plates arranged in the grid formation; and resin that is provided between the X-ray blocking plates and is configured to hold the X-ray blocking plates. In this situation, the X-ray blocking plates are examples of the first scattered ray eliminating part and the second scattered ray eliminating part.

Figure 3:
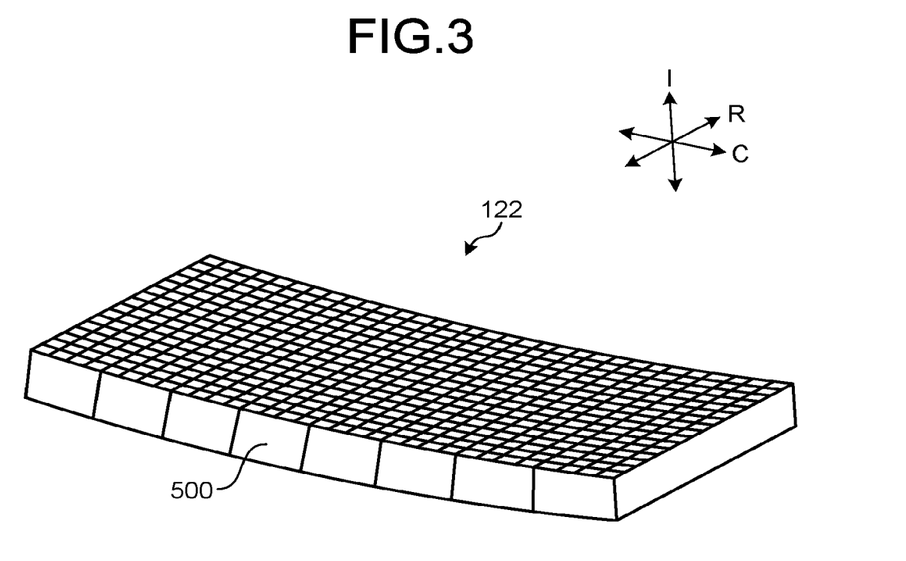
FIG. 3 is a drawing illustrating an exemplary configuration of a collimator according to the present embodiment.

FIG. 3 is a drawing illustrating an exemplary configuration of the collimator 122 according to the present embodiment.

For example, as illustrated in FIG. 3, the collimator 122 is configured by using a plurality of collimator modules 500 arranged in an arc formation along the channel direction. In this situation, each of the collimator modules 500 can individually be replaced.

In the present example, the collimator modules 500 are arranged in the channel direction; however, possible arrangements of the collimator modules 500 are not limited to this example. For instance, it is also acceptable to structure the collimator 122 by further arranging, in the row direction, a plurality of the collimator modules 500 that are arranged in the channel direction.

Figure 4:
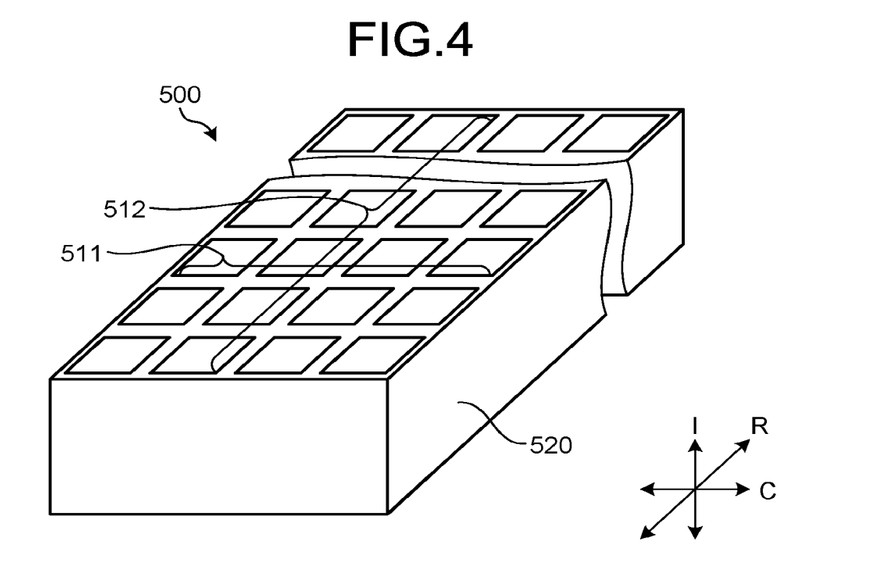
FIG. 4 is a drawing illustrating an exemplary configuration of any of collimator modules according to the present embodiment.

FIG. 4 is a drawing illustrating an exemplary configuration of any of the collimator modules 500 according to the present embodiment.

For example, as illustrated in FIG. 4, the collimator module 500 includes a plurality of X-ray blocking plates arranged in a grid formation along the channel direction and the row direction. More specifically, the collimator module 500 includes a plurality of X-ray blocking plates 511 arranged in the channel direction and a plurality of X-ray blocking plates 512 arranged in the row direction.

In this situation, the collimator module 500 is configured so that each of a plurality of slits (rectangular through holes) formed by the X-ray blocking plates arranged in the grid formation is arranged in a position corresponding, in one-to-one correspondence, to a different one of the scintillators and to a different one of the photodiodes included in one X-ray detection array 1211.

Possible arrangements of the X-ray blocking plates in the collimator modules 500 are not limited to this example. For instance, another arrangement is also acceptable in which each of the plurality of slits formed by the X-ray blocking plates arranged in the grid formation is provided for a different one of the rows of scintillators and photodiodes along the channel direction that are included in one X-ray detection array 1211.

Further, the collimator module 500 includes resin 520 that is provided between any two of the plurality of X-ray blocking plates arranged in the grid formation and is configured to hold the X-ray blocking plates.

In the present embodiment, to realize the collimator module 500 structured in this manner, the resin 520 has formed therein a plurality of groove-like slits arranged in a grid formation. The X-ray blocking plates are formed by pouring a filler containing metal particles into the slits and subsequently hardening the filler.

Figure 5:
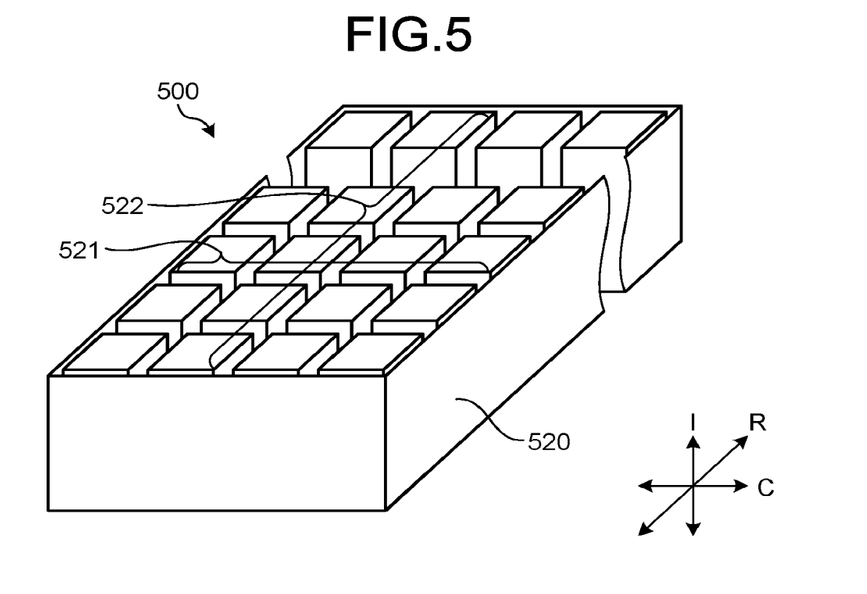
FIG. 5 is a drawing illustrating an exemplary configuration of resin included in the collimator module according to the present embodiment.

FIG. 5 is a drawing illustrating an exemplary configuration of the resin 520 included in the collimator module 500 according to the present embodiment.

For example, as illustrated in FIG. 5, the resin 520 has formed therein the plurality of groove-like slits arranged in the grid formation along the channel direction and the row direction. More specifically, the resin 520 has formed therein a plurality of slits 521 arranged in the channel direction and a plurality of slits 522 arranged in the row direction.

Further, by pouring the filler containing the metal particles into the slits formed in the resin 520 and subsequently hardening the filler, the plurality of X-ray blocking plates 511 arranged in the channel direction and the plurality of X-ray blocking plates 512 arranged in the row direction are formed.

In this situation, for example, the slits are formed by using a 3D printer. Alternatively, the slits may be formed through a grooving process using a blade. Examples of the metal particles contained in the filler include those of tungsten, molybdenum, tin, or the like.

By using this configuration, because the X-ray blocking plates are formed inside the slits formed in the resin 520, the X-ray blocking plates are held by the resin 520.

Ordinarily, when a collimator is structured with only X-ray blocking plates made of metal, there are problems where it would be difficult for the X-ray blocking plates to stand by themselves for being too thin or where it would be difficult to control deformation caused by rotation or vibration. In contrast, the structure described above solves these problems. In addition, while there is no need to use the structure of a correction plate or the like for internal R or external R, it is possible to shape the collimator by simply pouring the filler. It is therefore expected possible to improve throughput and yield.

In the present embodiment, the resin 520 included in the collimator module 500 may be formed to have various shapes.

FIGS. 6 to 12 are drawings illustrating various examples of the resin 520 included in the collimator module 500 according to the present embodiment.

For example, the resin 520 may be formed to have a hollow structure.

Figure 6:
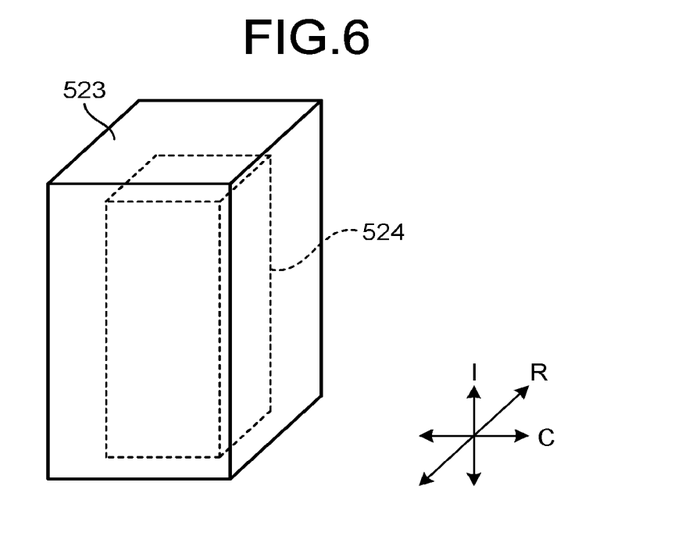
FIG. 6 is a drawing illustrating one of various examples of the resin included in the collimator module according to the present embodiment.

For instance, as illustrated in FIG. 6, in the resin 520, on the inside of each of a plurality of cubic parts 523 formed by the slits in the grid formation, a hole 524 opening to the side opposite from the X-ray incident side may be formed. In another example, on the inside of each of the plurality of cubic parts 523 formed by the slits in the grid formation, a plurality of slits may be formed. By forming the resin 520 to have the hollow structure as described herein, it is possible to inhibit attenuation of the primary component of the X-rays.

In yet another example, the resin 520 may further has a reinforcing part provided in a region of the hollow structure and configured to reinforce the resin 520.

Figure 7:
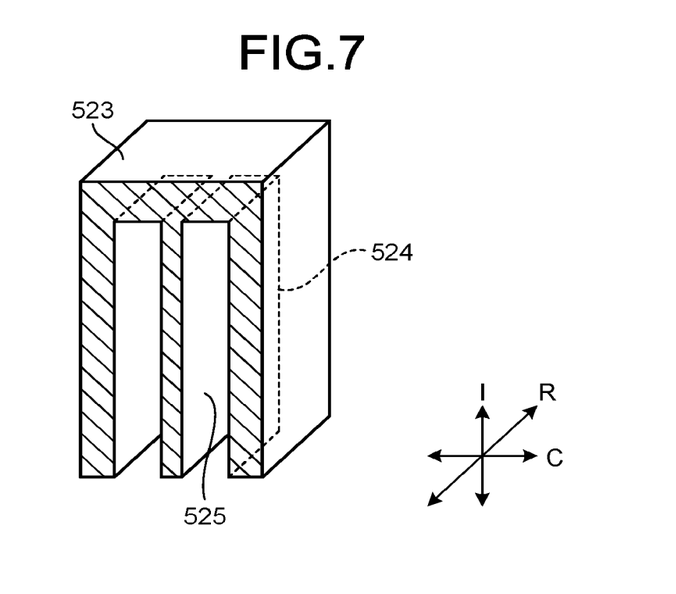
FIG. 7 is a drawing illustrating another one of the various examples of the resin included in the collimator module according to the present embodiment.

For example, as illustrated in FIG. 7, in the resin 520, the hole 524 formed on the inside of each of the plurality of cubic parts 523 formed by the slits in the grid formation may be provided with a plate-like reinforcing part 525. In that situation, for example, the reinforcing part 525 may be provided by configuring the hole 524 formed inside the cubic part 523 so as to have a shape having the reinforcing part 525. In yet another example, the reinforcing part 525 may be provided by attaching a plate-like member serving as the reinforcing part 525 to the hole 524 formed inside the cubic part 523.

In yet another example, the plurality of slits in the resin 520 may be formed along the X-ray incident direction.

Figure 8:
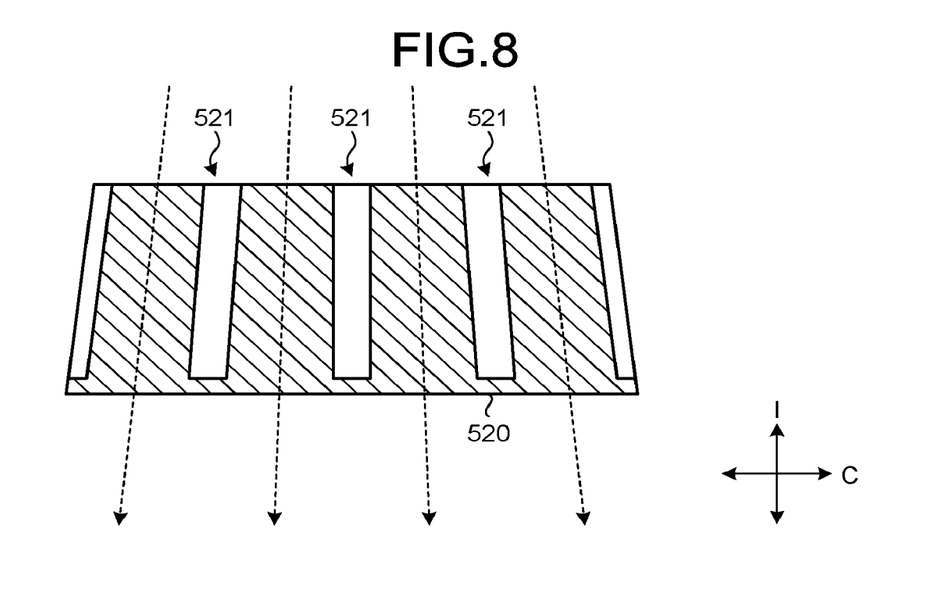
FIG. 8 is a drawing illustrating yet another one of the various examples of the resin included in the collimator module according to the present embodiment.

For example, as illustrated in FIG. 8, in the resin 520, the plurality of slits 521 arranged in the channel direction may each be formed so as to extend along the X-ray incident direction. In that situation, the slits 521 are formed in such a manner that the closer the slit is to the either end in terms of the channel direction, the larger is the slope angle. In yet another example, in the resin 520, the plurality of slits 522 arranged in the row direction may similarly be formed so as to each extend along the X-ray incident direction. By forming the slits in the resin 520 so as to extend along the X-ray incident direction as described herein, it is possible to form the X-ray blocking plates along the X-ray incident direction.

In yet another example, the resin 520 may be formed so that the depth varies among the grooves of the plurality of slits.

Figure 9:
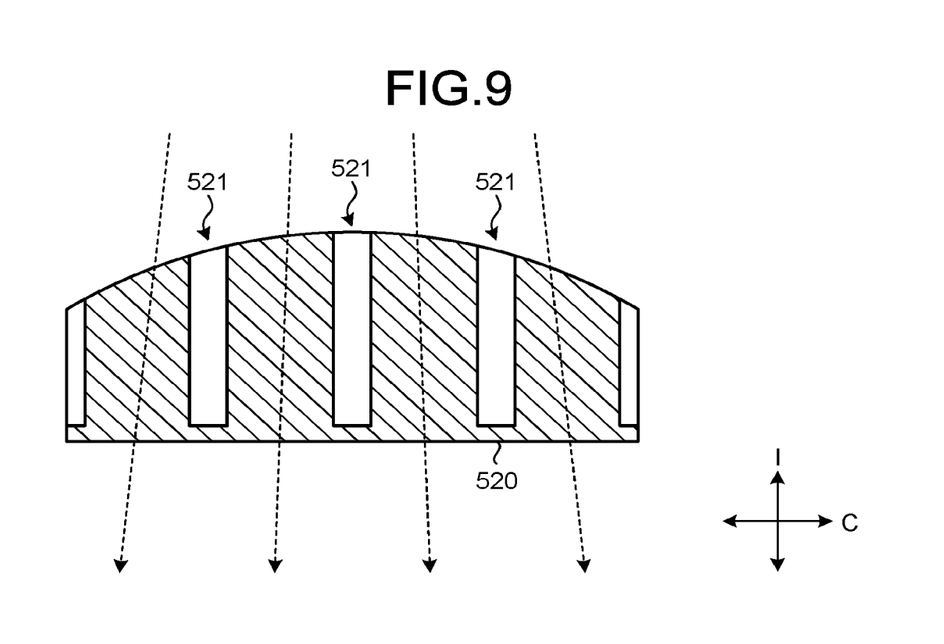
FIG. 9 is a drawing illustrating yet another one of the various examples of the resin included in the collimator module according to the present embodiment.

For example, as illustrated in FIG. 9, the resin 520 may be formed so that the thickness becomes smaller toward the either end in terms of the channel direction, and consequently, the closer the slit 521 is positioned to the either end in terms of the channel direction, the shallower is the depth of the groove. By varying the depth among the grooves of the slits in the manner described herein, it is possible to adjust the heights of the X-ray blocking plates as appropriate. It is therefore possible to easily control the capability of eliminating the scattered rays. For example, by varying the depth among the grooves of the slits in correspondence with the detecting elements (pixels), it is also possible to make the capabilities of eliminating the scattered rays the same as one another or different from one another, among the detecting elements.

In yet another example, the resin 520 may be formed so that the width varies among the grooves of the plurality of slits.

Figure 10:
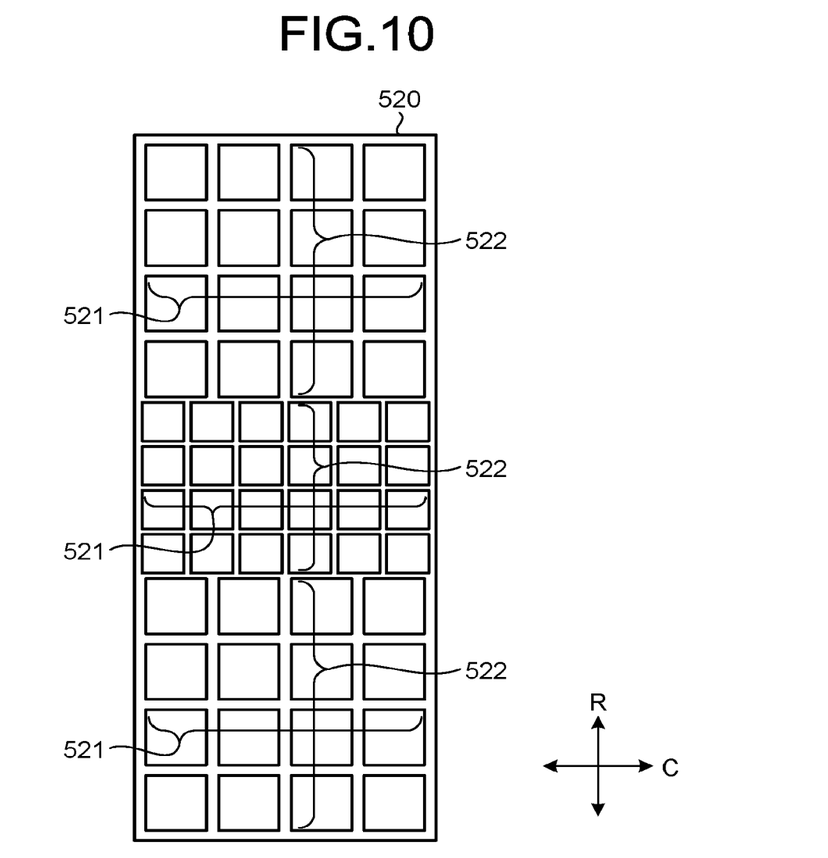
FIG. 10 is a drawing illustrating yet another one of the various examples of the resin included in the collimator module according to the present embodiment.

For example, as illustrated in FIG. 10, in the resin 520, in a range in the vicinity of the center in terms of the row direction, the width of each of the grooves and the intervals between the grooves of the slits 521 arranged in the channel direction and of the slits 522 arranged in the row direction may be smaller than those in a range positioned outside in terms of the row direction. As a result, in the range in the vicinity of the center in terms of the row direction, the widths of the X-ray blocking plates are smaller while the intervals between the X-ray blocking plates are also smaller, compared to those in the range positioned outside in terms of the row direction. Accordingly, even when the positional arrangements of the detecting elements included in the X-ray detector 12 have both highly detailed parts and normal resolution parts, it is possible to eliminate scattered rays appropriately for each of the detecting elements.

In yet another example, the resin 520 may be formed in such a manner that the pitch P of the slits 521 arranged in the channel direction is constant throughout the entire collimator 122.

In this situation, in the resin 520, the widths of the slits 521 positioned at the ends in terms of the channel direction are adjusted, so that the pitch P of the slits 521 is constant throughout the entire collimator 122 when the collimator modules 500 are arranged in the channel direction.

Figure 11:
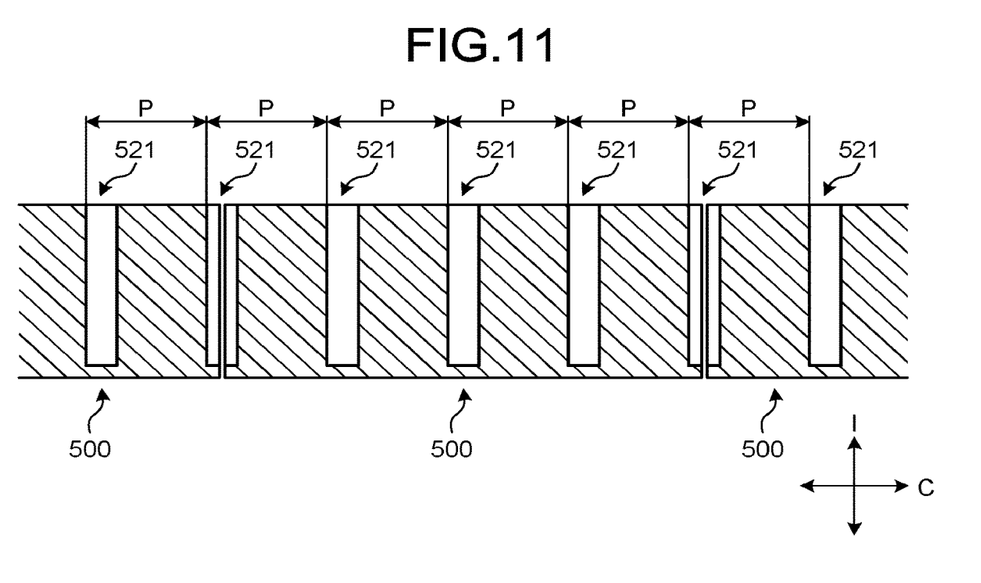
FIG. 11 is a drawing illustrating yet another one of the various examples of the resin included in the collimator module according to the present embodiment.

For example, as illustrated in FIG. 11, in the resin 520, when the slits 521 are provided at the two ends in terms of the channel direction, the slits 521 positioned at the two ends are each formed so as to have a width calculated by subtracting a half of the gap between the collimator modules 500 from a half of the width of each of the slits 521 positioned inside.

Figure 12:
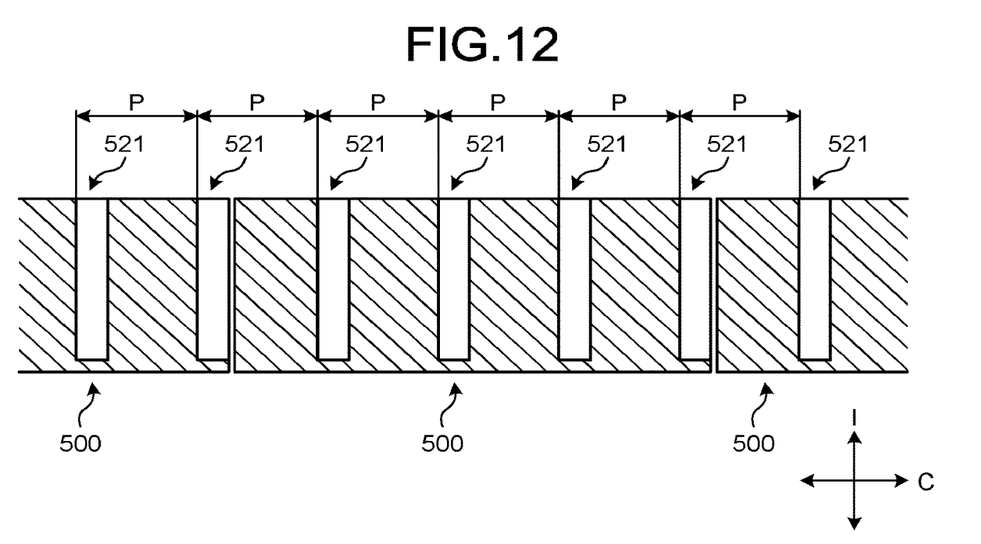
FIG. 12 is a drawing illustrating yet another one of the various examples of the resin included in the collimator module according to the present embodiment.

In yet another example, as illustrated in FIG. 12, in the resin 520, when the slits 521 are each provided at one end in terms of the channel direction, each of the slits 521 positioned at the one end is formed so as to have a width calculated by subtracting the dimension of the gap between the collimator modules 500 from the width of each of the slits 521 positioned inside.

As described above, in the present embodiment, the collimator 122 includes the plurality of collimator modules arranged at least in the one-dimensional direction. Further, each of the collimator modules includes the plurality of X-ray blocking plates and the resin that is provided between the X-ray blocking plates and is configured to hold the X-ray blocking plates.

According to this configuration, it is possible to easily manufacture the collimator 122 by implementing commonly-used techniques such as processing the resin and pouring the filler. Consequently, according to the present embodiment, it is possible to reduce the manufacturing costs of the collimator for use in an X-ray CT apparatus.

Further, according to the embodiment described above, because the X-ray blocking plates are held by the resin, it is possible to make the X-ray blocking plates thinner as the X-ray detector becomes highly detailed. Further, by varying the depth among the grooves of the slits formed in the resin, it is possible to easily control the scattered ray eliminating capabilities. Further, by forming the resin while using a 3D printer, it is possible to easily realize a complicated shape such as a two-dimensional collimator arranged on a spherical surface. In addition, by using the structure in which the spaces between the X-ray blocking plates are filled with the resin, it is possible to prevent the occurrence of artifacts that may be caused by unwanted substances entering the spaces between the X-ray blocking plates. Furthermore, there is no need to provide a structure for correcting deformation of the X-ray blocking plates. Also, because the manufacture of the collimator has a smaller workload, the manufacturing costs are lower. In addition, because it is possible to realize the present disclosure by combining together the commonly-used techniques, the costs for introducing this method are low. Furthermore, because the X-ray blocking plates are held by the resin, it is possible to reduce the artifacts that may be caused by rotation or vibration.

In the embodiments above, the example was explained in which the resin 520 remains in the collimator modules 500; however, another arrangement is also acceptable in which, to enhance utilization efficiency of the X-rays, the resin is removed by etching or the like, after the collimator modules 500 are formed, for example.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). When the processor is a CPU, for example, the processor realizes the functions by reading and executing the programs saved in a storage circuit. In contrast, when the processor is an ASIC, for example, the functions are directly incorporated in the circuit of the processor as a logic circuit, instead of the programs being saved in the storage circuit. Further, the processors in the present embodiments do not each necessarily have to be structured as a single circuit. It is also acceptable to structure one processor by combining together a plurality of independent circuits so as to realize the functions thereof. Further, it is also acceptable to integrate a plurality of the constituent elements illustrated in FIG. 1 into one processor so as to realize the functions thereof.

Further, the constituent elements of the apparatuses and devices illustrated in the drawings of the above embodiments and modification examples are based on functional concepts. Thus, it is not necessarily required to physically configure the constituent elements as indicated in the drawings. In other words, specific modes of distribution and integration of the apparatuses and devices are not limited to those illustrated in the drawings. It is acceptable to functionally or physically distribute or integrate all or a part of the apparatuses and devices in any arbitrary units, depending on various loads and the status of use. Further, all or an arbitrary part of the processing functions performed by the apparatuses and devices may be realized by a CPU and a program analyzed and executed by the CPU or may be realized as hardware using wired logic.

Furthermore, with regard to the processes explained in the embodiments and the modification examples described above, it is acceptable to manually perform all or a part of the processes described as being performed automatically. Conversely, by using a publicly-known method, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

According to at least one aspect of the embodiments described above, it is possible to reduce the manufacturing costs of the collimator for use in an X-ray CT apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A collimator for use in an X-ray CT apparatus, the collimator comprising:
   a collimator module including a first scattered ray eliminating part and a second scattered ray eliminating part; and
   resin provided between the first scattered ray eliminating part and the second scattered ray eliminating part so as to fill any space between the first scattered ray eliminating part and the second scattered ray eliminating part and configured to hold the first scattered ray eliminating part and the second scattered ray eliminating part.

2. The collimator according to claim 1, wherein the resin has a hollow structure.

3. The collimator according to claim 2, wherein, the resin further has a reinforcing part provided in a region of the hollow structure and configured to reinforce the resin.

4. The collimator according to claim 1, wherein a plurality of the collimator modules are arranged at least in a one-dimensional direction.

5. The collimator according to claim 1, wherein
   the resin has a first slit and a second slit formed therein and each shaped like a groove, and
   the first scattered ray eliminating part and the second scattered ray eliminating part are formed by pouring a filler containing metal particles into each of the first and the second slits and subsequently hardening the filler.

6. The collimator according to claim 5, wherein the first slit and the second slit are formed by using a 3D printer.

7. The collimator according to claim 5, wherein the first slit and the second slit are formed along an X-ray incident direction.

8. The collimator according to claim 5, wherein a depth varies among the grooves of the first slit and the second slit.

9. The collimator according to claim 5, wherein a width varies among the grooves of the first slit and the second slit.

10. A collimator module that is arranged at least in a one-dimensional direction and that structures a collimator for use in an X-ray CT apparatus, the collimator module comprising:
    a first scattered ray eliminating part;
    a second scattered ray eliminating part; and
    resin provided between the first scattered ray eliminating part and the second scattered ray eliminating part so as to fill any space between the first scattered ray eliminating part and the second scattered ray eliminating part and configured to hold the first scattered ray eliminating part and the second scattered ray eliminating part.

11. A collimator for use in an X-ray CT apparatus, comprising:
- a collimator module including a first scattered ray eliminating part and a second scattered ray eliminating part; and
- resin provided between the first scattered ray eliminating part and the second scattered ray eliminating part and configured to hold the first scattered ray eliminating part and the second scattered ray eliminating part,
- wherein the resin has a hollow structure.

12. A collimator for use in an X-ray CT apparatus, comprising:
- a collimator module including a first scattered ray eliminating part and a second scattered ray eliminating part; and
- resin provided between the first scattered ray eliminating part and the second scattered ray eliminating part and configured to hold the first scattered ray eliminating part and the second scattered ray eliminating part, wherein
- the resin has a first slit and a second slit formed therein and each shaped like a groove, and
- the first scattered ray eliminating part and the second scattered ray eliminating part are formed by pouring a filler containing metal particles into each of the first and the second slits and subsequently hardening the filler.

13. A collimator module that is arranged at least in a one-dimensional direction and that structures a collimator for use in an X-ray CT apparatus, the collimator module comprising:
- a first scattered ray eliminating part;
- a second scattered ray eliminating part; and
- resin provided between the first scattered ray eliminating part and the second scattered ray eliminating part and configured to hold the first scattered ray eliminating part and the second scattered ray eliminating part,
- wherein the resin has a hollow structure.

14. A collimator module that is arranged at least in a one-dimensional direction and that structures a collimator for use in an X-ray CT apparatus, the collimator module comprising:
- a first scattered ray eliminating part;
- a second scattered ray eliminating part; and
- resin provided between the first scattered ray eliminating part and the second scattered ray eliminating part and configured to hold the first scattered ray eliminating part and the second scattered ray eliminating part, wherein
- the resin has a first slit and a second slit formed therein and each shaped like a groove, and
- the first scattered ray eliminating part and the second scattered ray eliminating part are formed by pouring a filler containing metal particles into each of the first and the second slits and subsequently hardening the filler.

* * * * *